United States Patent [19]

Ward et al.

[11] Patent Number: 4,481,200
[45] Date of Patent: Nov. 6, 1984

[54] α₂-ADRENOCEPTOR ANTAGONISTIC BENZOQUINOLIZINES

[75] Inventors: Terence J. Ward, Slough; John F. White, Wokingham, both of England

[73] Assignee: John Wyeth & Brother, Limited, Maidenhead, England

[21] Appl. No.: 471,960

[22] Filed: Mar. 3, 1983

[30] Foreign Application Priority Data

Mar. 18, 1982 [GB] United Kingdom ............... 82/07970

[51] Int. Cl.³ .................. A61K 31/535; C07D 455/06
[52] U.S. Cl. ................................. 424/248.5; 424/258; 544/126; 546/95
[58] Field of Search .......................... 546/95; 544/126; 424/258, 248.5

[56] References Cited

U.S. PATENT DOCUMENTS 4,183,937 1/1980 Ward .................................. 424/258

OTHER PUBLICATIONS

Hamilton, C. et al., in *Frontiers in Hypertension Research* (Laragh et al., editors), Springer-Verlag, New York, 1981, pp. 348–352.

Primary Examiner—Richard A. Schwartz
Attorney, Agent, or Firm—George Tarnowski

[57] ABSTRACT

The invention concerns benzoquinolizines of formula

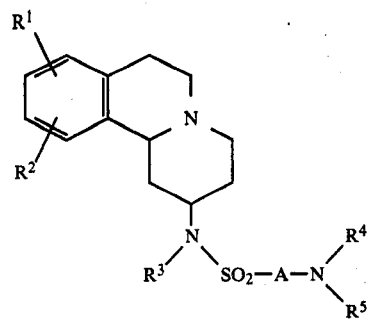

(I)

and their pharmaceutically acceptable acid addition salts. In the formula $R^1$ and $R^2$ which may be the same or different each represent hydrogen, lower alkyl, lower alkoxy or halogen, $R^3$ represents methyl or ethyl, A represents a direct bond between the S and N atoms or a lower alkylene group having 1 to 3 carbon atoms in the chain between the S and N atoms, $R^4$ and $R^5$ each independently represent hydrogen, lower alkyl, aryl or aryl(lower)alkyl or together with the nitrogen atom to which they are attached represent a five or six membered heterocyclic ring. The compounds possess α₂-adrenoceptor antagonistic activity and can be incorporated into pharmaceutical compositions.

9 Claims, No Drawings

α₂-ADRENOCEPTOR ANTAGONISTIC BENZOQUINOLIZINES

The invention relates to benzoquinolizines, to processes for preparing the benzoquinolizines, to their use and to pharmaceutical compositions containing them.

The novel compounds of the present invention are benzoquinolizines of the general formula (I)

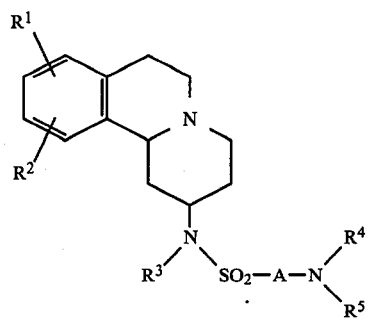

and their pharmaceutically acceptable acid addition salts. In formula (I), $R^1$ and $R^2$ which may be the same or different each represent hydrogen, lower alkyl, lower alkoxy or halogen, $R^3$ represents methyl or ethyl, A represents a direct bond between the S and N atoms or a lower alkylene group having 1 to 3 carbon atoms in the chain between the S and N atoms, $R^4$ and $R^5$ each independently represent hydrogen, lower alkyl, aryl or aryl(lower)alkyl or together with the nitrogen atom to which they are attached represent a five or six membered heterocyclic ring.

The term "lower" as used herein means that the radical referred to contains 1 to 6 carbon atoms. Preferably such radicals contain 1 to 4 carbon atoms. For example, a lower alkyl group may be methyl, ethyl, propyl or butyl. When $R^1$ and/or R represent lower alkoxy the group may be, for example, methoxy, ethoxy, propoxy or butoxy. When $R^1$ and/or $R^2$ represents halogen the substituent may be, for example, fluorine, chlorine or bromine. Preferably both $R^1$ and $R^2$ are hydrogen.

$R^3$ is preferably methyl.

When A is a direct bond the compounds of the invention are sulphonamido derivatives of the formula

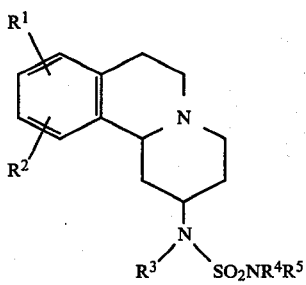

and the pharmaceutically acceptable acid addition salts thereof. When A is a lower alkylene group the group may be branched or straight chain provided that there are 1 to 3 carbon atoms in the chain between the S and N atoms. For example, the lower alkylene group may be methylene, ethylene, trimethylene or a branched chain group such as ethylethylene or propylene [—CH(CH₃).CH₂—].

When a radical, or part of a radical is referred to as "aryl" that radical or part of a radical is preferably a phenyl or substituted phenyl group. The substituted phenyl group can be a phenyl group substituted by one or more substituents chosen from, for example, halogen (e.g. chlorine, fluorine or bromine), alkoxy (e.g. lower alkoxy such as methoxy or ethoxy), lower alkyl (e.g. methyl, ethyl, propyl or butyl), alkylenedioxy (e.g. methylenedioxy or ethylenedioxy), amino, lower alkylamino, diloweralkylamino or trifluoromethyl.

Examples of $R^4$ and $R^5$ are hydrogen, lower alkyl (e.g. methyl, ethyl, propyl or butyl), aryl (e.g. phenyl or substituted phenyl as mentioned above) or aryl(lower)alkyl (e.g. benzyl or phenethyl in which the phenyl ring can be substituted as mentioned above). When $R^4$ and $R^5$ together with the N atom represent a five or six membered heterocyclic ring, the ring may be, for example, pyrrolidino, piperidino or morpholino.

The compounds of the invention may be prepared by reacting a reactive derivative of a sulphonic acid of formula (II)

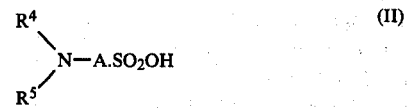

(where A, $R^4$ and $R^5$ are as defined above) with a 2-methylamino- or 2-ethylaminobenzoquinolizine of the general formula

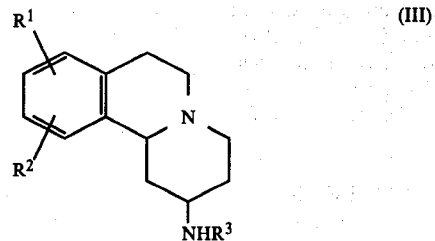

where $R^1$, $R^2$ and $R^3$ have the meanings given above and, if required, converting a free base into a pharmaceutically acceptable acid addition salt. The reactive derivative of the sulphonic acid can be, for example, the acid halide or anhydride. Preferably it is the acid halide i.e. a compound of formula (IV)

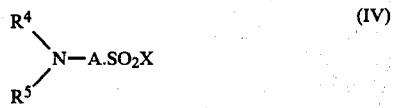

(where $R^4$, $R^5$ and A are defined above and X is halogen, preferably chlorine). The reaction is generally carried out under basic conditions. If necessary a reactive substituent group in a reactant may be protected during the reaction and the protecting group may be removed at a later stage. For example, where $R^4$ and $R^5$ are both hydrogen the primary amino group in the reactive derivative of the sulphonic acid may be protected as an acylated amino group (e.g. as a phthalimido group) and the acyl group removed subsequently by known methods.

An alternative method of preparing the compounds of the invention involves reaction of a benzoquinolizine of formula (V)

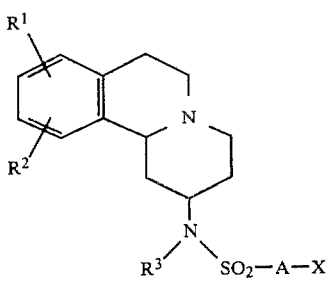

(where $R^1$, $R^2$, $R^3$ and A are as defined above and X is halogen, preferably chlorine) with ammonia or an amine of formula (VI)

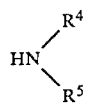

where $R^4$ and $R^5$ are as defined above. The starting materials of formula (V) in which A is lower alkylene, [which are described in the co-pending application Ser. No. 471,911 of Terence J. Ward entitled 'Benzoquinolizines' which is being filed on or about the same date as the instant application and which claims priority from U.K. application No. 8207943] may be prepared by, for example, reacting a reactive derivative of ω-haloalkanesulphonic acid with the benzoquinolizine of formula (III). The aminosulphonyl halide starting materials of formula (V) in which A is a direct bond may be prepared by halogenating the corresponding aminosulphonic acid.

A further method for preparing the compounds of the invention in which A is a direct bond comprises reaction of the benzoquinolizine of formula (III) with a sulphonamide derivative of formula

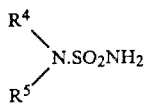

(where $R^4$ and $R^5$ have the meanings given above). Preferably the compound VII is sulphamide, i.e. the compound in which both $R^4$ and $R^5$ are hydrogen.

A preferred method for preparing certain compounds of the invention in which A is a lower alkylene group of at least two carbon atoms comprises adding ammonia or an amine of formula (VI) given to a benzoquinolizine of formula (VIII)

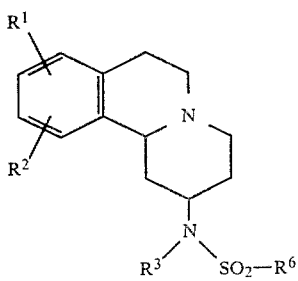

where $R^1$, $R^2$ and $R^3$ have the meanings given above and $R^6$ is a lower alkenyl group. A preferred lower alkenyl group is vinyl. The benzoquinolizines of formula (VIII) may be prepared by condensing a reactive derivative of an alkenesulphonic acid (e.g. the sulphonyl chloride) with an amine of formula (III). Alternatively the amine of formula (III) may be reacted with an appropriate ω-haloalkanesulphonyl chloride, particularly a β-haloethanesulphonyl chloride, under conditions basic enough to eliminate hydrogen chloride from the condensation product.

Compounds of the invention in which $R^4$ and/or $R^5$ are lower alkyl or aryl(lower)alkyl, in particular those compounds in which A is a lower alkylene group, may be prepared by alkylating or arylalkylating corresponding compounds in which $R^4$ and/or $R^5$ is hydrogen. The alkylation or arylalkylation may be carried out with, for example, a (lower)alkylhalide or aryl(lower)alkylhalide under basic conditions.

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compound.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The compounds of the invention possess two asymmetric carbon atoms and hence can exist in various stereochemical forms. In addition they can exist as cis or trans isomers. It will be realised that if the starting material of formula (III) is a mixture of isomers the product of formula (I) will also be a mixture of isomers unless the mixture is separated by standard procedures. The preferred compounds of the invention are the trans isomers in which the

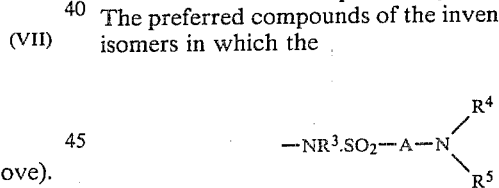

group is in the equatorial position, i.e. compounds of the general formula (IX)

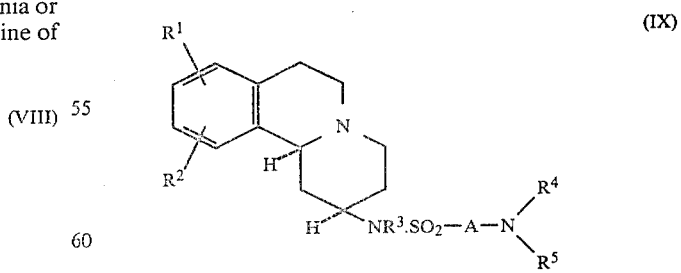

and the pharmaceutically acceptable acid addition salts thereof. These compounds can be prepared by the methods described above from the corresponding trans isomer starting material.

The compounds of the present invention possess pharmacological activity. In particular the compounds posses $\alpha_2$-adrenoceptor antagonistic activity in warm blooded animals and hence are of value in conditions where antagonism of the $\alpha_2$-adrenoceptor is desirable, for example, as antidepressants, in treatment of diabetes and in inhibiting blood platelet aggregation.

The compounds of the invention were tested for $\alpha_2$-adrenoceptor antagonistic activity on the rat field stimulated vas deferens preparation using a modification of the method of Drew, Eur. J. Pharmac., 1977, 42, 123–130. The procedure is described below.

Desheathed vasa deferentia from sexually mature rats were suspended in a 6 ml organ bath in Krebs solution at 37° and bubbled with 5% $CO_2$ in oxygen. Platinum ring electrodes were positioned above and below the tissue for field stimulation, The stimulus parameters being 0.1 Hz 1 ms pulse width at supramaximal voltage. Twitch responses were recorded isotonically with a 0.5 g loading. Clonidine hydrochloride was used as the $\alpha$-adrenoceptor agonist and cumulative concentration-response curves were constructed for the inhibition of twitch obtained with clonidine in the range 0.125 to 4 ng ml$^{-1}$. After washing out clonidine, the twitch response quickly recovered and an antagonist was then introduced into the Krebs reservoir. Clonidine concentration-response curves were repeated 90 min after introduction of the antagonist. The concentration of clonidine producing 50% inhibition of twitch before and after introduction of antagonist were obtained and the dose-ratio for clonidine was calculated. Various concentrations of the antagonists were used.

These results were plotted in the manner described by Arunlakshana & Schild, Br.J.Pharmac. Chemother., 1959, 14, 48–58 and the values of $pA_2$ and slope were calculated. The compounds of the invention possess potent $\alpha_2$-adrenoceptor antagonistic activity. The results are shown in the following Table I:

TABLE I

| Compound of Example | $pA_2$ ($\alpha_2$) |
|---|---|
| 1 | 7.44 |
| 2 | 7.4 |
| 3 | 7.26 |
| 4 | 7.43 |

The compounds of the invention antagonise the $\alpha_2$-adrenoceptors to a much greater extent than the $\alpha_1$-adrenoceptors. The $\alpha_1$ antagonistic activity can be evaluated by a number of different methods. One method involves assessing the activity on the isolated anococcygeus muscle of the rat. The method is based on that of Gillespie, Br.J.Pharmac., 1972, 45, 404–416. In the procedure male rats (250–360 g) are killed by a blow on the head and bled. The two anococcygeus muscles are removed from their position in the midline of the pelvic cavity, where they arise from the upper coccygeal vertebrae. The muscles are suspended in 5 ml organ baths in Krebs solution containing $10^{-4}$M ascorbic acid, to prevent drug oxidation. The tissues are gassed with a 95% oxygen, 5% $CO_2$ mixture and maintained at 37°. Longitudinal muscle contractions are recorded using isotonic transducers. Cumulative dose response curves are then obtained to phenylephrine or in some cases methoxamine, both agents being presynaptic alpha adrenoceptor agonists. The concentration range of phenylephrine or methoxamine used is 0.02 to 0.8 $\mu$g.ml$^{-1}$. The agonist is then washed from the bath and the test drug added to the bathing medium at a concentration of $10^{-6}$M. After 30 min equilibration with the test drug a further agonist dose response curve is obtained. The washing, equilibration and agonists dosing procedures are then repeated using $10^{-5}$M and $10^{-4}$M solutions of the test drug. Estimates of the $pA_2$ value for the test drug as an antagonist of phenylephrine or methoxamine were made from the agonist dose-ratios using the method of Arunlakshana & Schild, Br.J.Pharmac. Chemother., 1959, 14, 48–58.

The $pA_2$ for $\alpha_1$ antagonistic activity and the $\alpha_2/\alpha_1$ selectivity for compounds of the invention are given in Table II below.

TABLE II

| Compound of Example | $pA_2$ ($\alpha_1$) | $\alpha_2/\alpha_1$ selectivity* |
|---|---|---|
| 1 | 6.19 | 18 |
| 2 | 5.95 | 28 |
| 3 | 5.6 | 46 |
| 4 | 6.44 | 10 |

*antilog of ($\alpha_2 pA_2 - \alpha_1 pA_2$)

The invention further provides a compound of formula (I) or a pharmaceutically acceptable acid addition salt for use in antagonising $\alpha_2$-adrenoceptors in a mammal.

The invention also provides a pharmaceutical composition comprising a compound of general formula (II) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid ot a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The following Examples illustrate the invention:

EXAMPLE 1

N-Methyl-N-(1,3,4,6,7,11bα-hexahydro-2H-benzo[a]-quinolizin-2β-yl)-N'-methylsulphamide An ice-cold stirred solution of 2β-methylamino-1,3,4,6,7,11bα-hexahydro-2H-benzo[a]quinolizine (2.16 g) and triethylamine (1.2 g) in dichloromethane (25 cm$^3$) was treated with a solution of N-methylsulphamoyl chloride (1.30 g) in dichloromethane (25 cm$^3$). The clear solution was kept at room temperature for 3 days, washed with water (25 cm$^3$), then brine (25 cm$^3$) and dried (MgSO$_4$). Filtration and evaporation gave a yellow gum which was chromatographed on silica eluted with 10% ethanol-ethyl acetate to give a pale yellow gum (2.19 g). This was taken up in ethanol (5 cm$^3$), acidified with ethanolic HCl, diluted with ethyl acetate (25 cm$^3$) and filtered to give pale cream crystals.

Trituration with boiling ethanol gave pure title compound as the hydrochloride (2.19 g), very pale cream crystals, m.p. 205°–206° (dec).

EXAMPLE 2

N,N,N'-Trimethyl-N'-[1,3,4,6,7,11bα-hexahydro-2H-benzo[a]quinolizin-2β-yl]sulphamide An ice-cold stirred solution of 2β-methylamino-1,3,4,6,7,11b α-hexahydro-2H-benzo[a]quinolizine (2.16 g) and triethylamine (1.15 g) in dichloromethane (25 cm$^3$) was slowly treated with a solution of dimethylsulphamoyl chloride (1.44 g) in dichloromethane (25 cm$^3$). The clear solution was kept at room temperature for 2 days, when tlc showed that the reaction was essentially complete. The mixture was washed with water (2×25 cm$^3$), dried, filtered and evaporated to give a red-brown syrup (3.29 g). This was dissolved in ethanol (5 cm$^3$), acidified with ethanolic HCl, diluted with ethyl acetate (15 cm$^3$) and allowed to crystallise overnight. The crystals were collected by filtration and triturated with boiling methanol to give the title compound as the hydrochloride (2.19 g), colourless, short rods, m.p. 240°–248° (dec, decomposition and softening occurs over a wide range above 145°).

EXAMPLE 3

N-Methyl-N-(1,3,4,6,7,11bα-hexahydro-2H-benzo[a]-quinolizin-2β-yl)-2-dimethylaminoethanesulphonamide (a) An ice-cold, stirred solution of 2β-methylamino-1,3,4,6,7,11bα-hexahydro-2H-benzo[a]quinolizine (2.16 g) and triethylamine (1.2 g) in dichloromethane (25 cm$^3$) was slowly treated with a solution of 2-chloroethanesulphonyl chloride (1.63 g) in dichloromethane (25 cm$^3$). The clear solution was kept at room temperature for 3 days, then washed with aq NaHCO$_3$ and brine, and dried (MgSO$_4$). Filtration and evaporation gave a yellow gum which was chromatographed on silica eluted with 10% ethanol-ethyl acetate to give a yellow gum (1.56 g). This was dissolved in ethanol (5 cm$^3$), acidified with ethanolic HCl, diluted with ethyl acetate (7 cm$^3$) and cooled. The crystals were filtered off and washed with 10% ethanol-ethyl acetate to give N-methyl-N-(1,3,4,6,7,11bα-hexahydro-2H-benzo[a]-quinolizin-2β-yl)ethenesulphonamide, hydrochloride (1.58 g) as very pale cream crystals, with no clear m.p. (decomp. occurs above 190° causing liquefaction, no solid remains at 234°).

(b) The free base from (a) (1.18 g) was dissolved in 33% dimethylamine-ethanol solution (25 cm$^3$) and the clear solution kept at room temperature overnight. The solvents were evaporated, the residual oil taken up to hot ethanol (5 cm$^3$), acidified with ethanolic HCl, diluted with ethyl acetate (15 cm$^3$) and cooled. The crystals were filtered off and washed with ice-cold 20% ethanol-ethyl acetate, then dried at 80°/100 mm to give title compound as the dihydrochloride, hemihydrate (1.50 g), pale cream crystals, m.p. 258°–261° (dec).

EXAMPLE 4

N-(i-Propyl)-N'-(1,3,4,6,7,11bα-hexahydro-2H-benzo[a]quinolizin-2β-yl)-N'-methylsulphamide An ice-cold, stirred solution of 2β-methylamino-1,3,4,6,7,11bα-hexahydro-2H-benzo[a]quinolizine (2.16 g) and triethylamine (1.2 g) in dichloromethane (25 cm$^3$) was slowly treated with a solution of N-isopropylsulphamoyl chloride (1.58 g) in dichloromethane (15 cm$^3$). The clear solution was kept at room temperature for 1 day, washed with water (25 cm$^3$) and brine (25 cm$^3$) and dried (MgSO$_4$). Filtration and evaporation gave an organe syrup (3.53 g) which was chromatographed on silica and eluted with 10% ethanol-ethyl acetate to give a yellow syrup (3.19 g). This was taken up in hot ethanol (10 cm$^3$), acidified with ethanolic HCl, diluted with ethyl acetate (25 cm$^3$) and cooled. The crystals which separated overnight were collected by filtration and recrystallised from methanol to give pure title compound as the hydrochloride, hemimethanolate (1.55 g), colourless crystals, m.p. 170°–173° (dec.).

EXAMPLE 5

N-Methyl-N-sulphamido-1,3,4,6,7,11b-hexahydro-2H-benzo[a]quinolizin-2β-amine A mixture of 2β-methylamino-1,3,4,6,7,11bα-hexahydro-2H-benzo[a]quinolizine (4.64 g) and sulphamide (2.61 g) in 1,2-dimethoxyethane (50 cm³) was stirred and heated to reflux for 17 hours. After cooling, the supernatent liquid was decanted from some red gum and evaporated in vacuo. The residue was dissolved in dichloromethane and allowed to stand. After several hours the precipitated crystals were filtered off and washed with dichloromethane and water. The crystals were triturated with boiling ethanol, cooled and refiltered to give the title compound as colourless crystals, m.p. 190°–192° (dec.).

The crystals were suspended in hot ethanol (10 cm³), acidified with ethanol HCl and cooled. The gummy solid which initially formed crystallised after re-heating and cooling and was filtered to give the title compound as the hydrochloride (2.49 g), colourless crystals, m.p. 200°–202° (dec.).

EXAMPLE 6

N-Methyl-N-(1,3,4,6,7,11bα-hexahydro-2H-benzo[a]quinolizin-2β-yl)-2-aminoethanesulphonamide (a) 2-Phthalimidoethanesulphonyl chloride (1.65 g) was added over 2 min to a stirred mixture of 2β-methylamino-1,3,4,6,7,11bα-hexahydro-2H-benzo[a]quinolizine (1.24 g), triethylamine (1.2 cm³), and dichloromethane (15 cm³). After stirring for a further 2 hours the solution was washed with sodium carbonate solution, then dried and evaporated. Chromatography on neutral Woelm alumina with dichloromethane as eluent gave 1.53 of pure crystalline base, N-(1,3,4,6,7,11b-hexahydro-2H-benzo[a]quinolizine-2β-yl)-2-(1H-isoindole-1,3-dione-2-yl)-N-methylethanesulphonamide. The base was dissolved in ethanol (15 cm³) and p-toluenesulphonic acid hydrate (0.7 g) added to precipitate the salt as a gum, the mixture was warmed to re-dissolve the sum and then allowed to cool slowly to give the crystalline p-toluenesulphonate, hemihydrate, m.p. 137°–139°.

(b) A mixture of hydrazine hydrate (0.7 ml), the phthalimidosulphonylbenzoquinolizine from part (a) (4.55 g, 0.01 ml), and ethanol (30 ml) was heated at reflux for 1 hour. The mixture was initially a suspension but on heating cleared then partly crystallised. The solvent was then removed by evaporation, the residue was dissolved in water, basified with ammonia, and extracted with chloroform. The extract was dried and evaporated to yield the title compound as an oil (3.4 g). A sample (1 g) was dissolved in ethanol (10 cm³) and acidified by addition of p-toluenesulphonic acid hydrate to precipitate the di-p-toluenesulphonate salt, m.p. 210° C.

We claim:

1. A compound selected from the group consisting of a benzoquinolizine of the formula

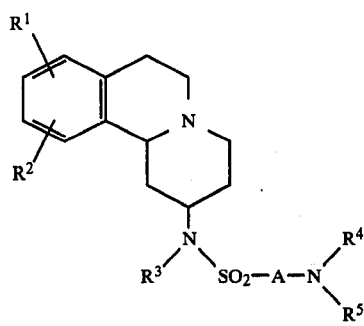

and a pharmaceutically acceptable acid addition salt thereof, wherein $R^1$ and $R^2$ each represent hydrogen, lower alkyl, lower alkoxy or halogen, $R^3$ represents methyl or ethyl, A represents a direct bond between the S and N atoms or a lower alkylene group having 1 to 3 carbon atoms in the chain between the S and N atoms, $R^4$ and $R^5$ each independently represent hydrogen, lower alkyl, phenyl, phenyl loweralkyl, substituted phenyl or substituted phenyl loweralkyl wherein the phenyl substituents are selected from one or more of halogen, lower alkyl, lower alkoxy, lower alkylenedioxy, amino, mono- or di-lower alkylamino or trifluoromethyl, or $R^4$ and $R^5$ together with the nitrogen atom to which they are attached form a pyrrolidino, piperidino or morpholino ring.

2. A compound according to claim 1 which is N-methyl-N-(1,3,4,6,7,11bα-hexahydro-2H-benzo[a]quinolizin-2β-yl)-N'-methylsulphamide or a pharmaceutically acceptable acid addition salt thereof.

3. A compound according to claim 1 which is N,N,N'-trimethyl-N'-[1,3,4,6,7,11bα-hexahydro-2H-benzo[a]quinolizin-2β-yl]sulphamide or a pharmaceutically acceptable acid addition salt thereof.

4. A compound according to claim 1 which is N-methyl-N-(1,3,4,6,7,11bα-hexahydro-2H-benzo[a]quinolizin-2β-yl)-2-dimethylaminoethanesulphonamide or a pharmaceutically acceptable acid addition salt thereof.

5. A compound according to claim 1 which is N-(i-propyl)-N'-(1,3,4,6,7,11bα-hexahydro-2H-benzo[a]quinolizin-2β-yl)-N'-methylsulphamide or a pharmaceutically acceptable acid addition salt thereof.

6. A compound according to claim 1 which is N-methyl-N-sulphamido-1,3,4,6,7,11bα-hexahydro-2H-benzo[a]quinolizin-2β-amine or a pharmaceutically acceptable acid addition salt thereof.

7. A compound according to claim 1 which is N-methyl-N-(1,3,4,6,7,11bα-hexahydro-2H-benzo[a]quinolizin-2β-yl)-2-aminoethanesulphonamide or a pharmaceutically acceptable acid addition salt thereof.

8. A pharmaceutical composition having $\alpha_2$-adrenoceptor antagonistic activity comprising an amount effective to antagonise $\alpha_2$-adrenoceptors of a compound selected from the group consisting of a benzoquinolizine of the formula

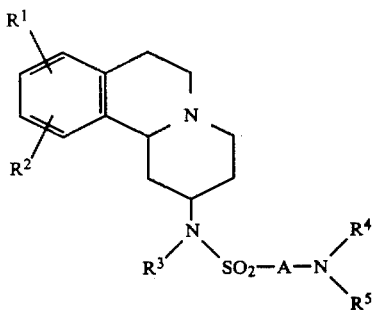

and a pharmaceutically acceptable acid addition salt thereof, wehrein $R^1$ and $R^2$ each represent hydrogen, lower alkyl, lower alkoxy or halogen, $R^3$ represents methyl or ethyl, A represents a direct bond between the S and N atoms or a lower alkylene group having 1 to 3 carbon atoms in the chain between the S and N atoms, $R^4$ and $R^5$ each independently represent hydrogen, lower alkyl, phenyl, phenyl loweralkyl, substituted phenyl or substituted phenyl loweralkyl wherein the phenyl substituents are selected from one or more of halogen, lower alkyl, lower alkoxy, lower alkylenedioxy, amino, mono- or di-lower alkylamino or trifluoromethyl, or $R^4$ and $R^5$ together with the nitrogen atom to which they are attached form a pyrrolidino, piperidino or morpholino ring.

9. A method of antagonising $\alpha_2$-adrenoceptors in warm blooded animals which comprises administering to the animal an effective amount of a compound selected from the group consisting of a benzoquinolizine of the formula

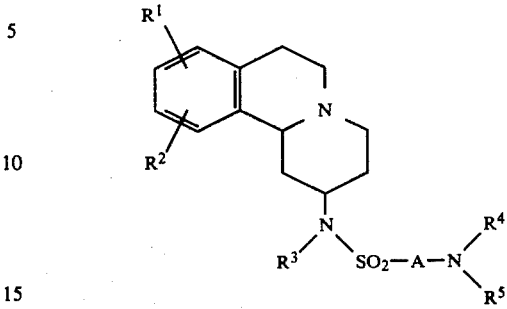

and a pharmaceutically acceptable acid addition salt thereof, wherein $R^1$ and $R^2$ each represent hydrogen, lower alkyl, lower alkoxy or halogen, $R^3$ represents methyl or ethyl, A represents a direct bond between the S and N atoms or a lower alkylene group having 1 to 3 carbon atoms in the chain between the S and N atoms, $R^4$ and $R^5$ each independently represent hydrogen, lower alkyl, phenyl, phenyl loweralkyl, substituted phenyl or substituted phenyl loweralkyl wherein the phenyl substituents are selected from one or more of halogen, lower alkyl, lower alkoxy, lower alkylenedioxy, amino, mono- or di-lower alkylamino or trifluoromethyl, or $R^4$ and $R^5$ together with the nitrogen atom to which they are attached form a pyrrolidino, piperidino or morpholino ring.

* * * * *